United States Patent [19]

Ishii et al.

[11] Patent Number: 5,414,137

[45] Date of Patent: * May 9, 1995

[54] PROCESS FOR PREPARING CARBONYL COMPOUNDS

[75] Inventors: Hirotoshi Ishii; Masanori Tsuzuki; Yoshinori Saito, all of Chiba, Japan

[73] Assignee: Idemitsu Kosan Company Limited, Tokyo, Japan

[*] Notice: The portion of the term of this patent subsequent to Aug. 17, 2010 has been disclaimed.

[21] Appl. No.: 67,803

[22] Filed: May 27, 1993

[30] Foreign Application Priority Data

May 29, 1992 [JP] Japan .................................. 4-138785

[51] Int. Cl.$^6$ .............................................. C07C 45/34
[52] U.S. Cl. .................................. 568/360; 568/401; 568/475
[58] Field of Search ........................ 568/360, 401, 457

[56] References Cited

U.S. PATENT DOCUMENTS

| | | | |
|---|---|---|---|
| 4,271,320 | 6/1981 | Tokitoh et al. | 568/401 |
| 4,310,704 | 1/1982 | Mimoun et al. | |
| 4,481,373 | 11/1984 | Okumura et al. | 568/401 |
| 4,532,362 | 7/1985 | Kukes et al. | 568/401 |
| 4,568,770 | 2/1986 | Alper et al. | 568/401 |
| 4,720,474 | 1/1988 | Vasilevskis et al. | |
| 4,723,041 | 2/1988 | Vasilenskis et al. | 568/401 |
| 5,103,064 | 4/1992 | Saito et al. | 568/401 |
| 5,237,103 | 8/1993 | Saito et al. | 568/360 |

FOREIGN PATENT DOCUMENTS

2638739 11/1990 France .

*Primary Examiner*—James H. Reamer
*Attorney, Agent, or Firm*—Armstrong, Westerman, Hattori, McLeland & Naughton

[57] ABSTRACT

An improved process for preparing carbonyl compounds by oxidizing olefins is disclosed. The process comprises oxidizing an olefin with oxygen or an oxygen containing gas in the presence of a palladium compound or metallic palladium, a polyoxoanion compound and an organic phosphorus compound in a solvent selected from oxygen-containing organic compounds, sulfur-containing organic compounds and nitrogen-containing organic compounds. In this process, precipitating of the palladium component is prevented and the high, reaction rate is well maintained through the prolonged reaction period and thus carbonyl compounds can be produced with high efficiency and productivity.

15 Claims, 1 Drawing Sheet

FIG.1

PROCESS FOR PREPARING CARBONYL COMPOUNDS

BACKGROUND OF THE INVENTION

1. Field of the Invention

The present invention relates to a process for preparing carbonyl compounds, more particularly, to a process for efficiently and consistently preparing carbonyl compounds, which include ketones such as acetone, methyl ethyl ketone, methyl isobutyl ketone, cyclopentanone, etc. and aldehydes such as acetaldehyde, etc. by oxidizing olefins.

2. Description of the Prior Art

Organic carbonyl compounds, which include ketones such as acetone, methyl ethyl ketone, methyl isopropyl ketone, cyclopentanone, etc., are useful as solvents and primary chemicals, etc.

As a process for preparation of carbonyl compounds by direct oxidation of olefins, there is known the so-called Wacker process, in which a $PdCl_2$-$CuCl_2$ system is employed as a catalyst. The Wacker process has some defect such that the reaction rate remarkably decreases as the number of carbon atoms of the starting olefin materials increases, and the reactivity of the internal olefins is poor. Further, the Wacker process requires a relatively large quantity of active chlorinated compound so that it causes problems of corrosion of equipment, formation of by-product chlorinated compounds, and so on. Therefore, the Wacker process is industrially applicable only to the production of lower carbonyl compounds such as acetaldehyde and acetone.

Under the circumstances, recently several novel processes have been proposed, in which improvements by modification of the catalyst system and the solvent system are attempted.

Japanese Laid-Open Patent Publication (Kohyo) No. 63-500,923 proposes a process using a catalyst system in which a redox metal such as Cu, Fe, Mn or the like and/or a ligand such as acetonitrile or the like are added to a Pd-polyoxoanion system.

In this process, the addition of only one of the redox metal or the ligand does not remarkably improve the catalyst activity, that is, the improvement of the catalyst activity depends largely on the synergistic effect of the redox metal and the ligand. Hence, the process involves a problem that the catalyst system is complicated, and therefore, separation and recovery of the catalyst components are difficult as in conventional processes described hereinabove. Further, this process presents a serious problem that the catalyst components precipitate as the reaction proceeds, and thereby the reaction rate drops to a remarkable low level, although the reactivity in the initial stage of the reaction is relatively good.

Japanese Examined Patent Publication (Kokoku) no. 49-024451 discloses a process in which olefins are oxidized with oxygen using a Pd-phosphine complex or a Pt-phosphine complex.

In this process, the activity of the active catalyst species $Pd^{2+}$ is poor and regeneration thereof is insufficient, although the reaction catalytically proceeds. Also, the catalyst components precipitate at the early stage of the reaction and are deactivated.

French Patent Specification No. 2,638,739 discloses a process in which a Pd-$AgNO_3$-(phosphorus compound) system is used as a catalyst.

In this process, the catalyst activity is not so good and it is a problem that expensive $AgNO_3$ must be used as an oxidizing agent.

Japanese Laid-Open Patent Publication (Kokai) No, 55-92333 discloses a process in which a Pd-(phosphorus compound) complex and peroxide compound is used as a catalyst.

In this process, it is a problem that catalyst activity is poor and the oxidizing agent used such as a peroxide is expensive.

Further, U.S. Pat. No. 4,532,362 discloses a process, in which a Pd-(heteropolyacid or Cu)-(phase-transfer catalyst)-(perfluorodecaline) system is used with a hydrocarbon/water as a solvent.

This process has a defect that the catalyst activity is poor. In the specification, Pd-phosphine complex is referred to but nothing is described concerning the effect thereof.

Further, Japanese Laid-Open Patent Publication (Kokai) No. 3-106844, a process for preparing carbonyl compounds characterized by oxidizing chain olefins in the presence of a Pd compound and a polyoxoanion compound in a solvent comprising alcohols. This process is satisfactory in that the initial activity of the catalyst is excellent and the high catalyst activity is well maintained over a long period of reaction of no less than 2 hours as described in the working examples in the specification.

In this technical field, however, recently a demand has arisen for a catalyst which can maintain catalyst activity for the reaction time far longer than that described in the above described patent.

The above-described process using the catalyst system comprising a Pd-compound and a polyoxoanion compound is superior to the Wacker process in which a large quantity of active chlorine compounds ($CuCl_2$, HCl, etc.) in that problems of corrosion of the apparatuses and formation of chlorinated by-products is reduced and there is an expectation of further improvement in catalyst activity and olefin reactivity. However, the process is not free from the above described various problems and thus cannot yet commercially employable. Therefore, development of a new process which solves the above described problems and practically applicable has been strongly desired.

We made an intensive study to solve the above problems and we found that deterioration of the catalyst activity caused by precipitating of Pd can be prevented and the catalyst performance and high reaction rate can be stably maintained by conducting the reaction in the co-presence of an organic phosphorus compound when carbonyl compounds are prepared by oxidation of olefins using a catalyst system comprising a palladium compound and a polyoxoanion compound such as heteropolyacid.

It was found that this process is remarkably advantageous since the process does not require use of a large quantity of the polyoxoanion compound, is free from apparatus corrosion, and separation of the product from the reaction system, and recovery and recycling of the solvent and the catalyst or the components thereof are easy.

Therefore, the object of the present invention is to solve the above-described problems and provide a process for preparing carbonyl compounds (aldehydes, ketones, etc.) by oxidation of olefins using a catalyst system comprising a palladium compound and/or a palladium metal and a polyoxoanion compound such as a heteropoly- or isopolyacid, etc., wherein deterioration of the catalyst activity of the Pd catalyst caused by precipitating of the catalyst component in the form of palladium black is prevented, the catalyst activity is well maintained and thus the object carbonyl compound is prepared with high efficiency and high productivity.

SUMMARY OF THE INVENTION

We came to complete this invention on the basis of our above-described findings.

The present invention is a process for preparing carbonyl compounds comprising reacting an olefin and oxygen or an oxygen-containing gas in at least one solvent selected from a group consisting of oxygen-containing organic compounds, sulfur-containing organic compounds and nitrogen-containing organic compounds, which may contain water, in the presence of a palladium compound and/or palladium metal, a polyoxoanion compound and an organic phosphorus compound.

DISCLOSURE OF THE INVENTION

Palladium Compounds and Metallic Palladium

Any compound which contains Pd as its metallic component can be used as the above described palladium compound. All palladium compounds conventionally used in this technical field can be used without any restriction.

Specific examples are: (1) inorganic salts of palladium such as palladium sulfate, palladium nitrate, palladium carbonate, etc.; halides such as palladium chloride, palladium bromide, etc.; palladate salts such as sodium tetrachloropalladate, sodium tetrabromopalladate, potassium tetrachloropalladate, potassium tetrabromopalladate, etc.; other inorganic palladium compounds such as palladium hydroxide, palladium oxide, etc.; (2) inorganic complexes such as ammine complex compounds $Pd(NH_3)_4Cl_2$, $Pd(NH_3)_2Cl_4$, etc.; (3) organic palladium compounds including organic acid salts such as palladium acetate palladium acetylacetonate ($Pd(AcAc)_2$), alkyl palladium, etc.; (4) organic complexes including palladium nitrile complexes such as $Pd(CH_3CN)_2Cl_2$, $Pd(PhCN)_2Cl_2$, wherein Ph stands for a phenyl group, etc.; other organic complexes such as Pd(EDTA), wherein EDTA means ethylene diamine tetraacetate, $Pd(COD)Cl_2$, wherein COD means cyclooctadiene, etc.; (5) palladium-containing polyoxoanion compounds such as palladium salts of heteropolyacid, palladium salts of isopolyacid etc.

Of these, from the viewpoint of activity in oxidation reaction, palladium compounds, in which palladium is in the bivalent state, i.e. the oxidation number is +2, are preferred and especially inorganic acid salts such as $PdSO_4 \cdot 2H_2O$, organic complexes, especially organic acid salts such as palladium acetate, are preferred.

These palladium compounds may be anhydride or may contain crystallization water. They can be used in the form of aqueous solution, organic solvent solution, suspension, etc. as well as being supported on a carrier such as activated carbon, etc. and in many other forms. There is no limitation in palladium compounds and any known palladium compound can be used. Also these palladium compounds can be used singly or as a combination of two or more or in the form of a compound or a composition.

In the present invention, metallic palladium can be used instead of the above-described palladium compounds or in combination therewith, as per se or carried on a support. All known forms of palladium can be used with out any restriction.

Polyoxoanion Compounds

Any polyoxoanion compound can be used without any restriction if it is able to convert the Pd reduced in the catalyst cycle to an oxidized form, especially to $Pd^{2+}$ and the thus formed reduced polyoxoanion itself can easily be re-oxidized by an oxidizing agent such as oxygen.

The polyoxoanion of the above-mentioned polyoxoanion compounds may be those which contain one or more of V, Mo, W, Nb, Ta, etc. Either of heteropolyoxoanion and isopolyoxoanion can be used. Of the polyoxoanions, when they contain one metal, those containing Mo or V are preferred and when they contains two or more metals, those containing Mo and V, Mo and W or V and W are preferred, and further those containing three of Mo, W and V are also preferred.

Heteropolyoxoanions means polyoxoanions which contain another hetero atom such as P, Si, As, Ge, B, Se, Te, etc. in their skeleton structure.

Of the heteropolyoxoanions usable in the process of the present invention, heteropolyoxoanions containing P as a hetero atom is preferable although those containing other hetero atoms can be used as well.

Examples of the preferred polyoxoanions are heteropolyoxoanions such as:
$(PMo_{12}O_{40})^{3-}$, $(PV_2Mo_{10}O_{40})^{5-}$, $(PV_3Mo_9O_{40})^{6-}$, $(PV_4Mo_8O_{40})^{7-}$, $(PV_6Mo_6O_{40})^{9-}$, $(PMo_6W_6O_{40})^{3-}$, $(P_2VMo_2W_{15}O_{62})^{7-}$, $(P_2VMo_5W_{12}O_{62})^{7-}$, etc. and isopolyoxoanions such as:
$(V_3Mo_3O_{19})^{5-}$, $(V_2Mo_6O_{26})^{6-}$, $(V_4Mo_8O_{36})^{4-}$, $(V_6Mo_6O_{36})^{6-}$,
$(V_8Mo_4O_{36})^{8-}$, $(V_2Mo_3W_7O_{36})^{2-}$, etc.

Examples of the above-described polyoxoanion compounds are compounds comprising one of the above described heteropolyoxoanions or isopolyoxoanions and one or more of cations (counter cations), that is, heteropolyacid or salts thereof or isopolyacid or salts thereof.

These polyoxoanion compounds may contain crystallization water. The cation components or counter cations are for example, $H^+$, $NH_4^+$, $Li^+$, $Na^+$, $K^+$, $Rb^+$, $Cs^+$, $Cu^{2+}$, $Ag^+$, $Pd^{2+}$, $Rh^{3+}$, etc. Among these, $H^+$ is most preferred.

There are many polyoxoanion compounds in accordance with variety of polyoxoanions as described and combination with counter ions as described. They are all usable in the present invention. However, from the viewpoint of catalyst activity, heteropolyacids which consist of a heteropolyoxoanion and $H^+$.

Specific examples of preferred heteropolyacids are: $H_3(PMo_{12}O_{40})$, $H_5(PV_2Mo_{10}O_{40})$, $H_6(PV_3Mo_9O_{40})$, $H_7(PV_4Mo_8O_{40})$, $H_9(PV_6Mo_6O_{40})$, $H_{11}(PMo_4V_8O_{40})$, $H_3(PMo_6W_6O_{40})$, $H_7(P_2VMo_2W_{15}O_{62})$, $H_7(P_2VMo_5W_{1262})$. etc.

These polyoxoanion compounds such as heteropolyacids may be anhydride or may contain crystallization water. They can be used as the starting material for preparation of the catalyst in various forms such as aqueous solution, organic solvent solution, suspension, or supported on a carrier such as activated carbon, etc. These polyoxoanion compounds can be used singly or in combination of two or more in the form of a mixture, a compound or a composition.

Organic Phosphorus Compounds

The point of the present invention is the co-presence of an organic phosphorus compound when carbonyl compounds are prepared using a catalyst composition comprising one of the above-described palladium compounds or palladium metal and one of the above-described polyoxoanion compounds.

Any of the above-described phosphorus compounds can be used as a phosphorus compound in the present invention without any restriction.

However, phosphines and phosphine oxides are especially preferred.

Specific examples of preferred phosphine compounds are: triarylphosphines, the aromatic rings of which may be substituted with at least one of alkyl groups and halogen atoms, such as triphenyl phosphine, tri(o-tolyl)-phosphine, tri-(p-tolyl)phosphine, tri-(m-tolyl)phosphine, tri-(o-chlorophenyl)phosphine, tri-(p-chlorophenyl)-phosphine and tri-(m-chlorophenyl)phosphine, etc.; trialkylphosphines such as trimethylphosphine, triethylphosphine, tri-(n-propyl)phosphine, tri(isopropyl)phosphine, tri(n-butyl)phosphine, tri-isobutylphosphine, tri-(sec-butyl)phosphine, etc.; tricycloalkylphosphines such as tricyclohexylphosphine, etc.; bis(-diarylphosphino)-alkanes such as bis(diphenylphosphino)methane, 1,2-bis(diphenylphosphino)-ethane, 1,3-bis(diphenylphosphino)propane, 1,4-bis-(diphenylphosphino)butane, etc.; sodium diphenylphosphinobenzene-m-sulfonate, etc.

Specific examples of preferred phosphine oxide compounds are: triarylphosphine oxides, the aromatic rings of which may be substituted with at least one of alkyl groups and halogen atoms, such as triphenylphosphine oxide, tri-(o-tolyl)phosphine oxide, tri-(p-tolyl)phosphine oxide, tri-(m-tolyl)phosphine oxide, tri-(o-chlorophenyl)phosphine oxide, tri-(p-chlorophenyl)phosphine oxide, tri-(m-chlorophenyl)phosphine oxide, etc.; trialkylphosphine oxides such as trimethylphosphine oxide, triethylphosphine oxide, tri-(n-propyl)phosphine oxide, tri-(iso-propyl)phosphine oxide, tri-(n-butyl)phosphine oxide, tri-(iso-butyl)-phosphine oxide, tri-(sec-butyl)-phosphine oxide, etc.; and tricycloalkylphosphine oxide such as tricyclohexyl phosphine oxide, etc.; and oxidized compounds of the above phosphines.

The above organic phosphorus compounds can be used singly or in combination of two or more.

In the preparation of carbonyl compounds in accordance with the present invention, at least one of the above-described palladium compounds, at least one of the above-described polyoxoanion compounds and at least one of the above-described organic phosphorus compounds are used. These can be mixed before they are supplied to the reaction system or can be separately supplied thereto. The organic phosphorus compounds can be added to the reaction system in the form of a complex with said palladium compounds such as Pd(PPh$_3$)$_4$, Pd(OAc)$_2$(PPh$_3$)$_2$, PdCl$_2$(PPh$_3$)$_2$, wherein Ph stands for a phenyl group. When palladium salts of heteropolyacids or isopolyacids are used, they can be used as polyoxoanion compounds, as palladium compounds or as both of them.

Quantities of Catalyst Components

The ratio of said polyoxoanion compound to said palladium component, i.e., palladium compound and/or metallic palladium, can be suitably determined depending upon species to be employed, although the ratio usually is 0.5–1,000 mol, more preferably, 1–600 mol polyoxoanion compound per mol palladium component.

If the quantity of the polyoxoanion is less than 0.5 mol per mol palladium component, the re-oxidation of the reduced palladium component cannot be satisfactorily effected in the catalyst cycle and the high level catalyst activity may not be maintained. On the other hand, if the quantity thereof is in excess, of 1,000 mol per mol palladium component, undesirable by-products are easily formed and the process becomes economically disadvantageous.

If desired, other promoters such as ligand components can be suitably added to the catalyst insofar as it does not adversely affect the intended object of the present invention.

The ratio of said phosphorus compound to said palladium component can be suitably determined usually in the range of 0.001–50 mol, preferably 0.01–10 mol per mol palladium component.

If the quantity of the phosphorus compound is less than 0.001 mol per mol palladium component, the effect of the addition of the phosphorus compound is not exhibited and if the quantity is in excess of 50 mol per mol palladium component, the induction period of the reaction is prolonged and thus the catalyst activity per unit time is reduced.

In the present invention, the three components, the palladium compound, the polyoxoanion compound and the phosphorus compound can be used in a homogeneous condition, a heterogeneous condition, or a combined condition of homogeneous and heterogeneous states when the reaction is conducted in one of the above described solvent or said solvent and water. For instance, the three components can be made into a homogeneous solution by dissolving them in one of the above-described solvent or a mixture of said solvent and water; only one of the three components is dissolved in said solvent; or one of the three components is dispersed in the solvent. Or, one or more of the three components can be supported or immobilized on a suitable carrier such as activated carbon, silica, polymer particles, etc.

Solvent

One of the features of the present invention is that preparation of carbonyl compounds by oxidation of olefins is conducted in at least one organic solvent selected from oxygen-containing organic compounds, sulfur-containing organic compounds and nitrogen-containing organic compounds, or in one of them which contains water.

Examples of said oxygen-containing organic compounds are ethers, alcohols, ketones, esters, etc.

Examples of said sulfur-containing organic compounds are dimethyl sulfoxide, sulfolane, etc. Examples of said nitrogen-containing organic compounds are N,N-dimethyl formamide, nitrobenzene, etc.

In the present invention, oxygen-containing organic compounds are preferred.

Preferred examples of the oxygen-containing organic compounds are, as for ethers, cyclic ethers such as 1,4-dioxane, teterahydrofuran, ethyleneglycol-dimethylether, diethyleneglycol-dimethylether, etc.

Of these ethers, cyclic ethers, especially 1,4-dioxane, tetrahydrofuran and the like are most preferred.

Preferred examples of the above-described alcohols are $C_{1-6}$ monohydric alcohols such as methanol, ethanol, n-propanol, isopropanol, n-butanol, sec-butanol, n-pentanol, n-hexanol, etc.

Preferred examples of the above-described ketones are acetone, methylethylketone, diethylketone, etc.

Preferred examples of the above-described esters are γ-butylolactone, δ-valerolactone, etc. These intramolecular esters are especially preferable.

These ethers, alcohols, ketones and esters can be used singly or in combination of two or more as a mixed solvent.

In the present invention, said organic solvent or a mixed solvent comprising said organic solvent to which water is added, can be used for the oxidation of olefin compounds.

When an organic solvent system containing water is used, the solubility of the catalyst components, especially polyoxoanion compounds is enhanced and the catalyst works more efficiently.

The quantity of the solvent used is not specifically limited. The amount to dissolve the catalyst components suffices although it is usually 1-10,000 liters, preferably 10-5,000 liters per mol palladium compound.

The mixing ratio of the organic solvent and water is also not specifically limited. A suitable ratio will be determined by considering the following factors. That is, the preferable mixing ratio of the organic solvent and water varies depending upon species of the palladium compounds, polyoxoanion compounds, organic phosphorus compounds, olefins as starting materials, and organic solvents; mode of reaction; reaction conditions and it cannot be determined by a simple rule. When the water content is too low, the reaction rate may drop for some reasons relating to the reaction mechanism or relating to the lower of the catalyst component. On the other hand, when the water content is excessively high, sufficient reaction rate may not be attained for the following reasons. That is, the Pd component may precipitate as metallic palladium ($Pd^0$) or coagulate causing deterioration of the catalyst activity; solubility of olefins, which are scarcely soluble in water, is reduced inviting poor contact efficiency of olefin as the starting material and the catalyst or the catalyst liquid especially in the case of a liquid phase reaction; and thus sufficient reaction rate cannot be attained. When these factors are considered, it is preferable that the water content in the solvent system is suitably selected within the range of 0.1-50 vol %.

Olefins as Starting Materials

In the process of the present invention, olefins are generally usable insofar as they have an olefinic double bond (C=C) or bonds. That is, not only monoolefins but also dienes, trienes, etc. having a plurality of olefinic double bonds can be used. The olefins may be terminal olefins which have a double bond or bonds at an end or ends of the molecule, internal olefins which have a double bond or bonds in the interior of the molecule or olefins which have C=C bonds both at an end or ends and in the interior of the molecule.

The usable olefins include not only chain olefins such as chain alkenes, chain alkadienes but also cyclic olefins such as cycloalkenes, cycloalkadienes; olefins having cyclic substituents such as cycloalkyl, aromatic ring, etc.

The number of the carbon atoms of olefins to be used is not specifically limited and therefore it is not less than 2. However, it is usually 2-20 and preferably 2-10 or thereabout.

The chain olefins can be of straight chain or of branched chain and specific examples are monoolefins including ethylene, propylene, 1-butene, trans-2-butene, cis-2-butene, isobutene, 1-pentene, 2-pentene, isopentenes such as 3-methyl-1-butene, 2-methyl-2-butene; 1-hexene, 2-hexene, 3-hexene, etc.; isohexenes such as 3-methyl-1-pentene, 4-methyl-1-pentene, 4-methyl-2-pentene, etc.; neohexene, 1-heptene, 2-heptene, 3-heptene, etc.; isoheptenes such as 4-methyl-1-hexene, etc.; 1-octene, 2-octene, 3-octene, 4-octene, isooctene, etc., 2-nonene, isononene, 1-decene, 2-decene, 3-decene, 4-decene, 5-decene, isodecene, undecene, dodecene, tridecene, tetradecene, hexadecene, etc.; and dienes such as pentadiene, hexadiene, heptadiene, octadiene, decadiene, etc.

Specific examples of the cyclic olefins are cycloalkenes such as cyclopentene, cyclohexene, cyclooctene, cyclodecene, etc.; those cycloalkenes and cycloalkadienes having substituents such as alkyl, etc.

The olefins having aromatic substituents are those chain olefins and cyclic olefins as listed above, which have aryl substituents such as phenyl, alkylphenyl, etc., typical examples of which are styrene compounds such as styrene, p-methylstyrene, β-methylstyrene, etc.

Examples of other cyclic olefins are vinylcyclohexane, vinylcyclohexene, allylcyclohexane, etc.

Of the above described olefins, examples of especially suitably used compounds are chain olefins having 2-20 carbon atoms including ethylene, propylene, 1-butene, trans-2-butene, cis-2-butene, 1-pentene, 2-pentene, isopentene, 1-hexene, 2-hexene, 3-hexene; isohexenes such as 4-methyl-1-pentene; neohexene, 1-heptene, 2-heptene, 1-octene, 2-octene, isooctene, etc. and cyclic olefins having 4-10 carbon atoms such as cyclopentene, cyclohexene, cyclooctene, etc. as well as styrenes.

Thus in the process of the present invention, high reactivity can be achieved not only for α-olefins but also for internal olefins such as 2-butene and cyclic olefins such as cyclopentene.

In the process of the present invention, although usually hydrocarbon olefins are used, the starting material are not always limited thereto but olefins containing a hetero atom or atoms can be applied.

In the present invention, the above-described olefins can be used singly or in combination of two or more. Also the starting material can contain other ingredients as long as they do not affect the process of the invention. Also the olefin starting material can be supplied to the reaction system as a mixture with water or a solvent.

The ratio of the used olefin to the catalyst depends on activity of the catalyst and other reaction conditions and, therefore, cannot be determined by a simple rule. But usually the ratio is within the range of 1-10,000 mol per mol palladium component. When this ratio is too small, the productivity per catalyst is low and thus the process is not economically employed. On the other hand, when this ratio is excessively large, sufficient conversion is not achieved or reaction time unduly prolonged and thus the productivity drops.

Oxidation

In the process of the present invention, carbonyl compounds are produced by the reaction of any of the above described olefins and oxygen or an oxygen-containing gas.

In the process of the present invention, as an oxidizing agent used for oxidation of the olefin, usually oxygen gas or a gas mixture, such as air, of oxygen, and a diluent gas are suitably used. As a diluent gas, although usually nitrogen is used, it is not limited thereto but helium, argon, carbon dioxide, etc. can be used. The oxygen or oxygen containing gases to be employed may contain other ingredients insofar as they do not affect the process of the present invention. Also these oxygen or oxygen containing gases can be supplied to the reaction system as a mixture with other component such as a portion of water or the solvent used.

The method of conducting the reaction is not specifically limited but batch process, semi-batch process, semi-continuous process, continuous circulation process, or combination of these processes can be employed.

As already described above, the three components of the palladium compound and/or metallic palladium, polyoxoanion compound and organic phosphorus compound can be used in various forms such as a homogeneous state in which all components are dissolved in a solvent, a state in which a portion of them is dissolved in the solvent and the remaining portions are dispersed in the solvent or in a heterogeneous solid state in which some components are supported or immobilized on a carrier or a polymer material.

The above-described olefins and solvents can be fed into the reaction system in the liquid state or the gaseous state. That is, various procedures are possible such as a liquid phase batch process in which a liquid mixture of said palladium compound, polyoxoanion compound, organic phosphorus compound and a solvent, which may contain an olefin, is allowed to react; a circulating process in which a gaseous olefin and oxygen or an oxygen containing gase are circulated through the above-mentioned liquid mixture; a circulating process in which an oxidizing gas is circulated through a liquid mixture of the olefin, said palladium compound, the polyoxoanion compound, the organic phosphorus compound and the solvent; a circulating process in which a, mixture of the palladium compound, the polyoxoanion compound, the organic phosphorus compound, the solvent, the olefin and the oxidizing agent is circulated; a gaseous phase circulation process in which a gaseous mixture of the gaseous olefin, the oxidizing agent, and vapor of the solvent is circulated through a carrier or a polymer material to which the palladium compound, the polyoxoanion compound, and the organic phosphorus compound are supported; etc.

In the case of a circulation process, the flow rate of the olefin or the oxidizing agent is not specifically limited, although usually it is suitably determined in the range of 10–5,000 mol/hour per mol palladium component.

The reaction temperature is usually selected within the range of 0°–200° C., preferably 20°–100° C. in the case of liquid phase reaction. At a temperature below 0° C., the reaction rate is too low and at a temperature in excess of 200° C., side reactions are liable to occur In the case of a gaseous phase reaction, the reaction temperature is suitably determined in the range of 50°–700° C., preferably 100°–500° C. At a temperature below 50° C. the reaction rate is insufficient and at a temperate over 700° C., side reactions are liable to occur.

The reaction pressure can be determined between normal pressure and high pressures, although it is usually suitably determined in the range of normal pressure to 100 kg/cm².

Reaction Product

As has been described above, carbonyl compounds such as aldehydes, ketones, etc. can be efficiently produced from corresponding olefins in accordance with the process of the present invention.

When ethylene is used as a starting material for instance, acetaldehyde is obtained. When propylene is used, acetone is obtained. When 1-butene, 2-butene or a mixture of these is used, methylethylketone is obtained. From 4-methyl-1-pentene, methylisobutylketone is obtained.

The thus obtained carbonyl compounds can be separated and purified by conventional procedures and can be recovered as a single compound of a desired purity or a mixture of a desired composition. When unreacted starting materials remain, these can be recovered and recycled to the reaction system. The used catalyst can be suitably regenerated or separated and reused as desired.

In the process of the present invention, carbonyl compounds can be obtained with a high yield and precipitating of the catalyst components is avoided.

The used solvents and accompanying substances, especially cyclic ethers, which are components thereof, can easily separated and recovered and, therefore, they can be used repeatedly as desired.

The thus obtained various carbonyl compounds can be suitably used as solvents, chemical reagents, raw materials for synthesis in various fields.

DESCRIPTION OF PREFERRED EMBODIMENTS

The invention will now be specifically described by way of working examples and comparative examples. However, the invention is not limited to these specific embodiments but can be practiced in modified and varied modes without deviating from the gist of the invention as claimed.

Example 1

Figure 1:
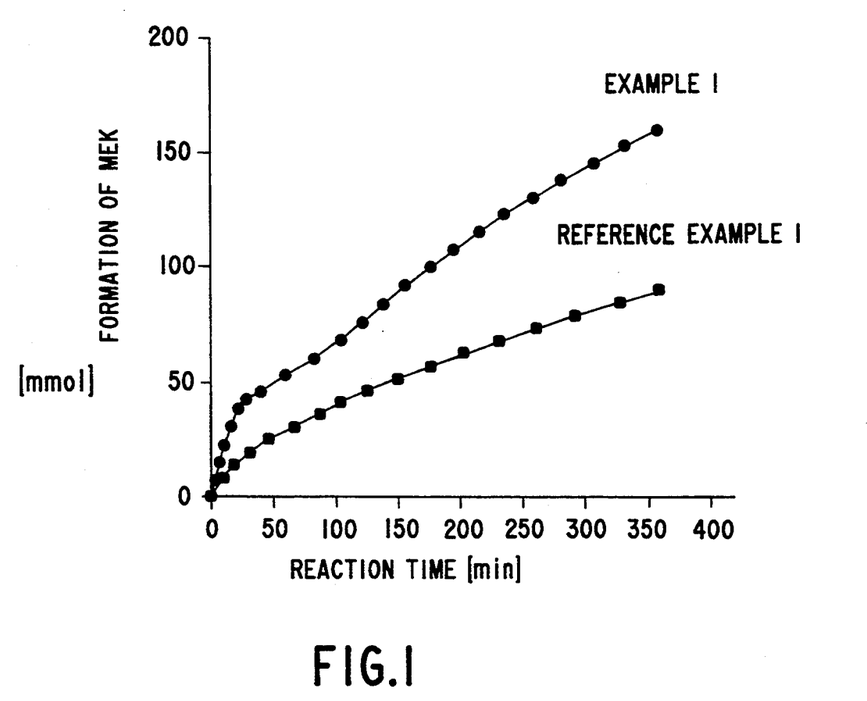
FIG. 1 is a graph which indicates the time course change of formation of MEK in Examples 1 and Reference Example 1.

In a mixture of 25 ml of 1,4-dioxane and 5 ml of water, 0.2 mmol (0.0527 g) of PdSO$_4$.2H$_2$O and 1.8 mmol (4.0819 g) H$_6$PV$_3$Mo$_9$O$_{40}$ (water content: 25.3 wt %) were dissolved and further 0.8 mmol (0.2098 g) of triphenylphosphine was added. The mixture was placed in an autoclave. 534 mmol of trans-2-butene and oxygen were charged into the autoclave and the mixture was allowed to react at 50° C. under a pressure of 8 kg/cm² (gauge), which was maintained by feeding oxygen, for 6 hours. Thus 138 mmol of methylethylketone (may be indicated as MEK hereinafter) was formed. In this case, the formation of MEK per hour, per mol palladium, i.e., the TOF (turnover frequency) with respect to MEK was 115 mol/(mol-Pd-hr). The time course change in MEK formation is shown in the attached FIG. 1. After the reaction was finished, no precipitate of the catalyst components was recovered. The reaction conditions are indicated in Table 1 and the results are indicated in Table 2.

Reference Example 1

In a mixture of 25 ml of 1,4-dioxane and 5 ml of water, 0.2 mmol (0.0527 g) of $PdSO_4 \cdot 2H_2O$ and 1.8 mmol (4.0819 g) $H_6PV_3Mo_9O_{40}$ (water content: 25.3 wt %) were dissolved. The mixture was placed into an autoclave. 538 mmol of trans-2-butene and oxygen were charged into the autoclave and the mixture was allowed to react at 50° C. under a pressure of 8 kg/cm² (gauge), which was maintained by feeding oxygen, for 6 hours. The time course change in MEK formation is shown in the attached FIG. 1. The reaction conditions are indicated in Table 1 and the results are indicated in Table 2.

Example 2

The procedures of Example 1 were repeated except that 5.4 mmol (12.2457 g) of $H_6PV_3Mo_9O_{40}$ was used and the reaction was conducted at 75° C. under a pressure of 10 kg/cm² (pressurized with oxygen). The reaction conditions are shown in Table 1 and the results are shown in Table 2.

Example 3

The procedures of Example 2 were repeated except that 360 mmol of trans-2-butene was used and the reaction was conducted for 3 hours. The reaction conditions are shown in Table 1 and the results are shown in Table 2.

Example 4

The procedures of Example 3 were repeated except that 0.1 mmol (0.0262 g) of triphenylphosphine was used. The reaction conditions are shown in Table 1 and the results are shown in Table 2.

Example 5

The procedures of Example 3 were repeated except that 0.8 mmol (0.2916 g) of sodium diphenylphosphinoben-zene-m-sulfonate was used instead of triphenylphosphine. The reaction conditions are shown in Table 1 and the results are shown in Table 2.

Example 6

The procedures of Example 3 were repeated except that 0.8 mmol (0.2435 g) of (o-tolyl)phosphine was used instead of triphenylphosphine. The reaction conditions are shown in Table 1 and the results are shown in Table 2.

Example 7

The procedures of Example 3 were repeated except that 20 ml of 1,4-dioxane and 10 ml of water were used. The reaction conditions are shown in Table 1 and the results are shown in Table 2.

Example 8

The procedures of Example 3 were repeated except that 0.1 mmol (0.0264 g) of $PdSO_4 \cdot 2H_2$ and 0.4 mmol (0.1048 g) of triphenylphosphine were used. The reaction conditions are shown in Table 1 and the results are shown in Table 2.

Example 9

The procedures of Example 3 were repeated except that 0.2 mmol (0.01498 g) of $Pd(OAc)_2(PPh_3)_2$, which is a triphenyl phosphine complex of Pd, instead of $PdSO_4 \cdot 2H_2O$ and triphenylphosphine. The reaction conditions are shown in Table 1 and the results are shown in Table 2.

Example 10

The procedures of Example 3 were repeated except that 1.8 mmol (5.0117 g) of $H_3PW_6Mo_6O_{40}$ (water content: 15.5%) instead of $H_6PV_3Mo_9O_{40}$. The reaction conditions are shown in Table 1 and the results are shown in Table 2.

Example 11

The procedures of Example 3 were repeated except that dimethylformamide was used instead of 1,4-dioxane. The reaction conditions are shown in Table 1 and the results are shown in Table 2.

Example 12

The procedures of Example 3 were repeated except that dimethylsulfoxide was used instead of 1,4-dioxane. The reaction conditions are shown in Table 1 and the results are shown in Table 2.

Example 13

The procedures of Example 3 were repeated except that γ-butyrolactone was used instead of 1,4-dioxane. The reaction conditions are shown in Table 1 and the results are shown in Table 2.

Example 14

The procedures of Example 3 were repeated except that MEK was used instead of 1,4-dioxane. The reaction conditions are shown in Table 1 and the results are shown in Table 2.

Example 15

The procedures of Example 3 were repeated except that 1-butene was used instead of trans-2-butene and the pressure was 8 kg/cm² (pressurized with oxygen). The reaction conditions are shown in Table 1 and the results are shown in Table 2.

Example 16

The procedures of Example 3 were repeated except that 178 mmol of 1-octene was used instead of trans-2-butene and the pressure was 8 kg/cm² (pressurized with an oxygen-containing gas($N_2/O_2$ by vol.=74/26)). The reaction conditions are shown in Table 1 and the results are shown in Table 2.

Example 17

The procedures of Example 16 were repeated except that cyclopentene was used instead of 1-octene. The reaction conditions are shown in Table 1 and the results are shown in Table 2.

Example 18

The procedures of Example 3 were repeated except that triphenylphosphine oxide was used instead of triphenylphosphine. The reaction conditions are shown in Table 1 and the results are shown in Table 2.

Example 19

The procedures of Example 18 were repeated except that tri(n-butyl)phosphine oxide was used instead of triphenylphosphine oxide. The reaction conditions are shown in Table 1 and the results are shown in Table 2.

Example 20

In a mixture of 100 ml of 1,4-dioxane and 20 ml of water, 0.025 mmol (0.0066 g) of $PdSO_4.2H_2O$ and 7.2 mmol (16.3276 g) of $H_6PV_3Mo_9O_{40}$ were dissolved and further 0.1 mmol (0.0262 g) of triphenylphosphine was added. The mixture was placed in an autoclave and 267 mmol of trans-2-butene and oxygen were charged into the autoclave and the reaction conducted at 80° C. and under a pressure of 8 kg/cm² (gauge, pressurized with oxygen) for 1 hour. The reaction conditions are shown in Table 1 and the results are shown in Table 2.

Example 21

The procedures of Example 20 were repeated except that the reaction temperature was 120° C. and the reaction time was 1 hour 30 minutes. The reaction conditions are shown in Table 1 and the results are shown in Table 2.

Example 22

The procedures of Example 20 were repeated except that 0.05 mmol (0.0132 g) of $PdSO_4.2H_2O$, 0.2 mmol (0.0525 g) of triphenylphosphine and 0.45 mmol (1.020 g) of $H_6PV_3Mo_9O_{40}$ (water content: 25.3 wt %) were used. The reaction conditions are shown in Table 1 and the results are shown in Table 2.

Example 23

In a mixture of 25 ml of 1,4-dioxane and 5 ml of water, 0.2 mmol (0.0527 g) of $PdSO_4.2H_2O$ and 1.8 mmol (4.0819 g) of $H_6PV_3Mo_9O_{40}$ were dissolved and further 0.8 mmol (0.1618 g) of tri(n-butyl)phosphine was added. The mixture was placed in an autoclave, which was preheated over 1 hour and 30 minutes. At 80° C., 267 mmol of trans-2-butene and oxygen were charged into the auto clave and the reaction was conducted under a pressure of 8 kg/cm² for 30 minutes. The reaction conditions are shown in Table 1 and the results are shown in Table 2.

Example 24

The procedures of Example 23 were repeated except that 0.05 mmol (0.1209 g) of Pd supported on silica powder modified with diphenylphosphinopropane was used instead of $PdSO_4.2H_2O$ and triphenylphosphine and the reaction was continued for 2 hours. The reaction conditions are shown in Table 1 and the results are shown in Table 2.

Comparative Example 1

In a mixture of 5 ml of acetonitrile and 25 ml of water, 0.2 mmol (0.0527 g) of $PdSO_4.2H_2O$ and 1.8 mmol (4.0819 g) of $H_6PV_3Mo_9O_{40}$ were dissolved, and further 2.0 mmol (0.4999 g) of $CuSO_4.5H_2O$ was added. The mixture was placed in an autoclave. 200 mmol of trans-2-butene and oxygen were charged into the autoclave. The mixture was allowed to react at 50° C. under a pressure of 6 kg/cm² (pressurized with oxygen) for 2 hours. The reaction conditions are shown in Table 1 and the results are shown in Table 2.

Comparative Example 2

In a mixture of 25 ml of 1,4-dioxane and 5 ml of water, 0.2 mmol (0.0527 g) of $PdSO_4.2H_2O$ and 0.8 mmol (0.2099 g) of triphenylphosphine were dissolved. The mixture was placed in an autoclave. 350 mmol of trans-2-butene and oxygen were charged into the autoclave. The mixture was allowed to react at 75° C. under a pressure of 8 kg/cm² (pressurized with oxygen) for 3 hours. The reaction conditions are shown in Table 1 and the results are shown in Table 2.

Comparative Example 3

In 30 ml of ethanol, 0.4 mmol (0.0709 g) of $PdCl_2$ and 2.0 mmol (0.3410 g of $CuCl_2.2H_2O$ were dissolved, and further 0.8 mmol (0.2099 g) of triphenylphosphine was added. The mixture was placed in an autoclave and 200 mmol of trans-2-butene and oxygen were charged into the autoclave. The mixture was allowed to react at 75° C. under a pressure of 8 kg/cm² (pressurized with oxygen) for 2 hours. The reaction conditions are shown in Table 1 and the results are shown in Table 2.

Comparative Example 4

In 30 ml of ethanol, 0.4 mmol (0.0709 g) of $PdCl_2$, and 2.0 mmol (0.3410 g) of $CuCl_2.2H_2O$ were dissolved and further 0.8 mmol (0.02099 g) of triphenylphosphine was added. The mixture was placed in an autoclave. 200 mmol of trans-2-butene and oxygen were charged into the autoclave. The mixture was allowed to react at 75° C. under a pressure of 6 kg/cm² (pressurized with oxygen) for 2 hours. The reaction conditions are shown in Table 1 and the results are shown in Table 2.

Comparative Example 5

In 25 ml of n-octane and 5 ml of water, 0.2 mmol (0.0527 g) of $PdSO_4.2H_2O$ and 1.8 mmol (4.0819 g) of $H_6PV_3Mo_9O_{40}$ were dissolved, and further 0.8 mmol (0.2099 g) of triphenyl phosphine was added. The mixture was placed in an autoclave. 270 mmol of trans-2-butene and oxygen were charged into the autoclave. The mixture was allowed to react at 75° C. under a pressure of 8 kg/cm² (pressurized with oxygen)a for 2 hours. The reaction conditions are shown in Table 1 and the results are shown in Table 2.

As described above in detail, in accordance with the present invention, precipitating of the catalyst components is prevented, the catalyst activity is well maintained at high level not only in the initial stage but all through the reaction period, and thus carbonyl compounds can be produced in a high yield with good productivity.

TABLE 1

| | Reaction Conditions | | | | | | |
|---|---|---|---|---|---|---|---|
| | Pd component Species Amount (mmol) | Organic Phosphorus Component Species Amount (mmol) | Polyoxoanion Component Species Amount (mmol) | Olefin Species Amount (mmol) | Solvent Species Amount (ml/ml) | Temp. (°C.) | Pressure (Kg/cm²) | Time (hour) |
| Example 1 | $PdSO_4$/0.2 | *1/0.8 | $H_6PV_3Mo_9O_{40}$/1.8 | 2-butene/534 | 1,4-dioxane/water (25/5) | 50 | 8 | 6 |
| Example 2 | $PdSO_4$/0.2 | *1/0.8 | $H_6PV_3Mo_9O_{40}$/5.4 | 2-butene/534 | 1,4-dioxane/water (25/5) | 75 | 10 | 6 |
| Example 3 | $PdSO_4$/0.2 | *1/0.8 | $H_6PV_3Mo_9O_{40}$/5.4 | 2-butene/360 | 1,4-dioxane/water (25/5) | 75 | 10 | 3 |
| Example 4 | $PdSO_4$/0.2 | *1/0.1 | $H_6PV_3Mo_9O_{40}$/5.4 | 2-butene/360 | 1,4-dioxane/water (25/5) | 75 | 10 | 3 |

TABLE 1-continued

Reaction Conditions

| | Pd component Species Amount (mmol) | Organic Phosphorus Component Species Amount (mmol) | Polyoxoanion Component Species Amount (mmol) | Olefin Species Amount (mmol) | Solvent Species Amount (ml/ml) | Temp. (°C.) | Pressure (Kg/cm$^2$) | Time (hour) |
|---|---|---|---|---|---|---|---|---|
| Example 5 | PdSO$_4$/0.2 | *2/0.8 | H$_6$PV$_3$Mo$_9$O$_{40}$/5.4 | 2-butene/360 | 1,4-dioxane/water (25/5) | 75 | 10 | 3 |
| Example 6 | PdSO$_4$/0.2 | *3/0.8 | H$_6$PV$_3$Mo$_9$O$_{40}$/5.4 | 2-butene/360 | 1,4-dioxane/water (25/5) | 75 | 10 | 3 |
| Example 7 | PdSO$_4$/0.2 | *1/0.8 | H$_6$PV$_3$Mo$_9$O$_{40}$/5.4 | 2-butene/360 | 1,4-dioxane/water (20/10) | 75 | 10 | 3 |
| Example 8 | PdSO$_4$/0.1 | *1/0.4 | H$_6$PV$_3$Mo$_9$O$_{40}$/5.4 | 2-butene/360 | 1,4-dioxane/water (25/5) | 75 | 10 | 3 |
| Example 9 | Pd (OAc)$_2$ (PPh$_3$)$_2$/0.2 | | H$_6$PV$_3$Mo$_9$O$_{40}$/5.4 | 2-butene/360 | 1,4-dioxane/water (25/5) | 75 | 10 | 3 |
| Example 10 | PdSO$_4$/0.2 | *1/0.8 | H$_3$PW$_6$Mo$_6$O$_{40}$/1.8 | 2-butene/360 | 1,4-dioxane/water (25/5) | 75 | 10 | 3 |
| Example 11 | PdSO$_4$/0.2 | *1/0.8 | H$_6$PV$_3$Mo$_9$O$_{40}$/5.4 | 2-butene/360 | dimethylformamide/water (25/5) | 75 | 10 | 3 |
| Example 12 | PdSO$_4$/0.2 | *1/0.8 | H$_6$PV$_3$Mo$_9$O$_{40}$/5.4 | 2-butene/360 | dimethylsulfoxide/water (25/5) | 75 | 10 | 3 |
| Example 13 | PdSO$_4$/0.2 | *1/0.8 | H$_6$PV$_3$Mo$_9$O$_{40}$/5.4 | 2-butene/360 | γ-butyrolactone/water (25/5) | 75 | 10 | 3 |
| Example 14 | PdSO$_4$/0.2 | *1/0.8 | H$_6$PV$_3$Mo$_9$O$_{40}$/5.4 | 2-butene/360 | MEK/water (25/5) | 75 | 10 | 3 |
| Example 15 | PdSO$_4$/0.2 | *1/0.8 | H$_6$PV$_3$Mo$_9$O$_{40}$/5.4 | 1-butene/360 | 1,4-dioxane/water (25/5) | 75 | 8 | 3 |
| Example 16 | PdSO$_4$/0.2 | *1/0.8 | H$_6$PV$_3$Mo$_9$O$_{40}$/5.4 | 1-octane/178 | 1,4-dioxane/water (25/5) | 75 | N$_2$/O$_2$ 8 | 3 |
| Example 17 | PdSO$_4$/0.2 | *1/0.8 | H$_6$PV$_3$Mo$_9$O$_{40}$/5.4 | cyclopentene/178 | 1,4-dioxane/water (25/5) | 75 | N$_2$/O$_2$ 8 | 3 |
| Example 18 | PdSO$_4$/0.2 | *4/0.8 | H$_6$PV$_3$Mo$_9$O$_{40}$/5.4 | 2-butene/360 | 1,4-dioxane/water (25/5) | 75 | 10 | 3 |
| Example 19 | PdSO$_4$/0.2 | *5/0.8 | H$_6$PV$_3$Mo$_9$O$_{40}$/5.4 | 2-butene/360 | 1,4-dioxane/water (25/5) | 75 | 10 | 3 |
| Example 20 | PdSO$_4$/0.025 | *1/0.1 | H$_6$PV$_3$Mo$_9$O$_{40}$/7.2 | 2-butene/267 | 1,4-dioxane/water (100/20) | 80 | 8 | 1 |
| Example 21 | PdSO$_4$/0.025 | *1/0.1 | H$_6$PV$_3$Mo$_9$O$_{40}$/7.2 | 2-butene/267 | 1,4-dioxane/water (100/20) | 120 | 8 | 1.5 |
| Example 22 | PdSO$_4$/0.05 | *1/0.2 | H$_6$PV$_3$Mo$_9$O$_{40}$/0.45 | 2-butene/267 | 1,4-dioxane/water (100/20) | 80 | 8 | 1 |
| Example 23 | PdSO$_4$/0.2 | *5/0.8 | H$_6$PV$_3$Mo$_9$O$_{40}$/1.8 | 2-butene/267 | 1,4-dioxane/water (25/5) | 80 | 8 | 0.5 |
| Example 24 | *6/0.05 | | H$_6$PV$_3$Mo$_9$O$_{40}$/0.05 | 2-butene/267 | 1,4-dioxane/water (25/5) | 80 | 8 | 2 |
| Ref. Ex. 1 | PdSO$_4$/0.2 | — | H$_6$PV$_3$Mo$_9$O$_{40}$/1.8 | 2-butene/538 | 1,4-dioxane/water (25/5) | 50 | 8 | 6 |
| Com. Ex. 1 | PdSO$_4$/0.2 | CuSO$_4$/2.0 | H$_6$PV$_3$Mo$_9$O$_{40}$/1.8 | 2-butene/200 | acetonitrile/water (5/25) | 50 | 6 | 2 |
| Com. Ex. 2 | PdSO$_4$/0.2 | *1/0.8 | — | 2-butene/350 | 1,4-dioxane/water (25/5) | 75 | 8 | 3 |
| Com. Ex. 3 | PdCl$_2$/0.4 | *1/0.8 | (CuCl$_2$/2.0) | 2-butene/200 | ethanol (30) | 75 | 8 | 2 |
| Com. Ex. 4 | PdCl$_2$/0.4 | *1/0.8 | (VOSO$_4$/2.0) | 2-butene/200 | ethanol (30) | 75 | 8 | 3 |
| Com. Ex. 5 | PdSO$_4$/0.2 | *1/0.8 | H$_6$PV$_3$Mo$_9$O$_{40}$/1.8 | 2-butene/200 | n-octane/water (20/5) | 75 | 8 | 2 |

*1 triphenylphosphine
*2 sodium diphenylphosphinobenzene-m-sulfonate
*3 tri(o-tolyl)phosphine
*4 triphenylphosphine oxide
*5 tri(n-butyl)phosphine
*6 Pd carried on silica modified with diphenylphophinopropane

TABLE 2

| | Results | | |
|---|---|---|---|
| | Product | Amount of Product [mmol] | TOF [mol/(mol-Pd · hr)] | Precipitate Recovered [g] |
| Example 1 | MEK | 138 | 115 | none |
| Example 2 | MEK | 162 | 135 | none |
| Example 3 | MEK | 160 | 266 | none |
| Example 4 | MEK | 174 | 290 | none |
| Example 5 | MEK | 185 | 308 | none |
| Example 6 | MEK | 80 | 133 | none |
| Example 7 | MEK | 128 | 214 | none |
| Example 8 | MEK | 98 | 326 | none |
| Example 9 | MEK | 158 | 263 | none |
| Example 10 | MEK | 98 | 163 | none |
| Example 11 | MEK | 115 | 192 | none |
| Example 12 | MEK | 125 | 208 | none |
| Example 13 | MEK | 108 | 180 | none |
| Example 14 | MEK | 128 | 213 | none |
| Example 15 | MEK | 152 | 254 | none |
| Example 16 | 2-octanone | 158 | 263 | none |
| Example 17 | cyclopentanone | 58 | 79 | none |
| Example 18 | MEK | 134 | 224 | none |
| Example 19 | MEK | 141 | 235 | none |
| Example 20 | MEK | 8 | 309 | none |
| Example 21 | MEK | 15 | 616 | none |
| Example 22 | MEK | 16 | 309 | none |
| Example 23 | MEK | 26 | 264 | none |
| Example 24 | MEK | 21 | 208 | none |
| Ref. Ex. 1 | MEK | 89 | 74 | none |
| Com. Ex. 1 | MEK | 51 | 63 | 0.0114 |
| Com. Ex. 2 | MEK | 4 | 7 | 0.0186 |
| Com. Ex. 3 | MEK | 8 | 20 | 0.0078 |
| Com. Ex. 4 | MEK | 2 | 3 | 0.0095 |
| Com. Ex. 5 | MEK | 1 | 3 | 0.0135 |

What we claim is:

1. In a method for the oxidation of olefins to carbonyl compounds by contacting the olefin with oxygen in a solvent in the presence of a palladium and polyoxoanion catalyst system, the improvement which comprises adding to the system an organophosphorus compound selected from the group consisting of triarylphosphines, trialkylphosphines, tricycloalkylphoshines, diphenylphosphinobenzenezulfonic acid salts, triarylphospine oxides, trialkylphosphine oxides and tricycloalkylphosphine oxides.

2. A process for producing a carbonyl compound which comprises oxidizing a straight or branched chain olefin having to 2 to 20 carbon atoms or a cyclic olefin having 4 to 10 carbon atoms at a temperature of 0°–200° C. and at a pressure of atmospheric pressure to 100 kg/cm$^2$ with oxygen or an oxygen containing gas in the presence at least one palladium component selected from the group consisting of metallic palladium and a palladium compound; a polyoxoanion compound containing as its metal component at least one metal selected from the group consisting of Mo, W, V, Nb and Ta; and an organic phosphorus compound selected from the group consisting of triarylphosphines, trialkylphosphines, tricycloalkylphosphine, diphenylphosphinobenzenezulfonic acid salts, triarylphosphine oxides, trialkylphosphine oxides and tricycloalkylphosphine oxides in an organic solvent selected from the group consisting of ethers, alcohols, ketones, esters, dimethyl sulfoxide, sulfolane, N,N-dimethylformamide and nitrobenzene.

3. A process for preparing carbonyl compounds as claimed in claim 2, wherein said polyoxanion compound is at least one compound selected from the group consisting of $H_3$, $H_5$, $H_6$, $H_7$, $H_9$, $H_{11}$, $H_3$, $H_7$ and $H_7$.

4. A process for preparing carbonyl compounds as claimed in claim 3, wherein said polyoxanion compound is at least one compound selected from the group consisting of $H_6$ and $H_3$.

5. A method according to claim 2, wherein the solvent contains water.

6. A process for preparing carbonyl compounds as claimed in claim 2, wherein said palladium compound is at least one selected from a group consisting of inorganic palladium compounds, inorganic complexes of palladium, organic palladium compounds, organic complexes of palladium and palladium-containing polyoxoanion compounds.

7. A process for preparing carbonyl compounds as claimed in claim 6, wherein said palladium compound is an inorganic palladium compound.

8. A process for preparing carbonyl compounds as claimed in claim 7, wherein said palladium compound is at least one selected from a group consisting of palladium sulfate and palladium chloride.

9. A process for preparing carbonyl compounds as claimed in claim 2, wherein said polyoxoanion compound is at least one selected from a group consisting of hetropolyacids and isopolyacids.

10. A process for preparing carbonyl compounds as claimed in claim 2, wherein said polyoxoanion compound is used in an amount of 0.5–1,000 mol per mol of the palladium component.

11. A process for preparing carbonyl compounds as claimed in claim 2, wherein said polyoxoanion compound is used in an amount of 1–600 mol per mol of the palladium component.

12. A process for preparing carbonyl compounds as claimed in claim 2, wherein said organic phosphorus compound is used in an amount of 0.001–50 mol per mol of the palladium component.

13. A process for preparing carbonyl compounds as claimed in claim 2, wherein said organic phosphorus compound is used in an amount of 0.01–10 mol per mol palladium component.

14. A process for preparing carbonyl compounds as claimed in claim 2, wherein said organic solvent is used in an amount of 1–10,000 liters per mol of the palladium component.

15. A process for preparing carbonyl compounds as claimed in claim 2, wherein said organic solvent is used in an amount of 10–5,000 liters per mol of the palladium component.

* * * * *